(12) United States Patent
Hajjar et al.

(10) Patent No.: US 6,527,550 B1
(45) Date of Patent: Mar. 4, 2003

(54) APPARATUS AND METHOD FOR PRODUCING A DENTAL PROSTHETIC WITH A DEVICE HAVING A LINEAR ROTARY BEARING

(75) Inventors: Victor J. Hajjar, 1600 Galen Rd., Harrisburg, PA (US) 17112; John Robert Studer, Hummelstown, PA (US)

(73) Assignee: Victor J. Hajjar, Harrisburg, PA (US)

( * ) Notice: Subject to any disclaimer, the term of this patent is extended or adjusted under 35 U.S.C. 154(b) by 0 days.

(21) Appl. No.: 09/504,074

(22) Filed: Feb. 15, 2000

(51) Int. Cl.[7] .............................................. A61C 19/00
(52) U.S. Cl. ...................... 433/53; 433/222.1; 433/223; 409/124
(58) Field of Search ........................... 433/202.1, 212.1, 433/218, 222.1, 223, 76, 53; 29/896.1; 409/124

(56) References Cited

U.S. PATENT DOCUMENTS

| | | |
|---|---|---|
| 361,131 A | 4/1887 | Carlinet |
| 4,403,961 A | 9/1983 | Gurney |
| 4,789,649 A * | 12/1988 | Abert et al. .................... 501/3 |
| 5,135,393 A | 8/1992 | Eidenbenz et al. |
| 5,256,011 A * | 10/1993 | Taylor .......................... 409/92 |
| 5,313,740 A | 5/1994 | Eidenbenz et al. |
| 5,314,335 A | 5/1994 | Fung |
| 5,332,622 A | 7/1994 | Shoher et al. |
| 5,342,696 A | 8/1994 | Eidenbenz et al. |
| 5,383,752 A | 1/1995 | Rheinberger et al. |
| 5,813,859 A | 9/1998 | Hajjar et al. |
| 5,880,962 A * | 3/1999 | Andersson et al. .... 364/468.04 |
| 6,190,171 B1 * | 2/2001 | Hajjar et al. ................ 433/218 |

OTHER PUBLICATIONS

Where is the Gap? Machinable ceramic systems and conventional laboratory restorations at a glance, Sandro Siervo et al, Operative Dentistry, Quintessence International, vol. 25, No. 11/1994, pp. 773–779.
Fabrication of conversative ceramic restorations using copy–milling technology, Edward A. McLaren, DDS et al, 1994 Quintessence Publishing Co., Inc., Chicago, ILL. QDT 1994, pp. 19–25.
High–strength alumina crowns and fixed partial dentures generated by copy–milled technology, Edward A McLaren, DDS et al, 1995 Quintessence Publishing Co., Inc., Chicago, ILL. QDT 1995, pp. 31–38.
Brochure entitled "Introducing Celay Crowns", Vident, Baldwin Park, CA, 91706, L–9044V (undated).
Brochure entitled "CELAY, The Business Builder", Vident Baldwin Park, CA, 91706, l–9017V (undated).

* cited by examiner

Primary Examiner—Ralph A. Lewis
(74) Attorney, Agent, or Firm—Burns, Doane, Swecker & Mathis, LLP

(57) ABSTRACT

The present invention is directed to enhancing the accuracy with which tooth restorations are machined, using a device which can accurately copy mill a dental prosthetic blank from a previously formed dental prosthetic model, and which can closely replicate the feel of a dental tool to which dentists are accustomed. The device uses a tool supported on a linear rotary axis to mill the dental prosthetic blank. In addition, exemplary embodiments are directed to the preparation of a hybrid dental prosthetic blank which can be easily machined.

12 Claims, 12 Drawing Sheets

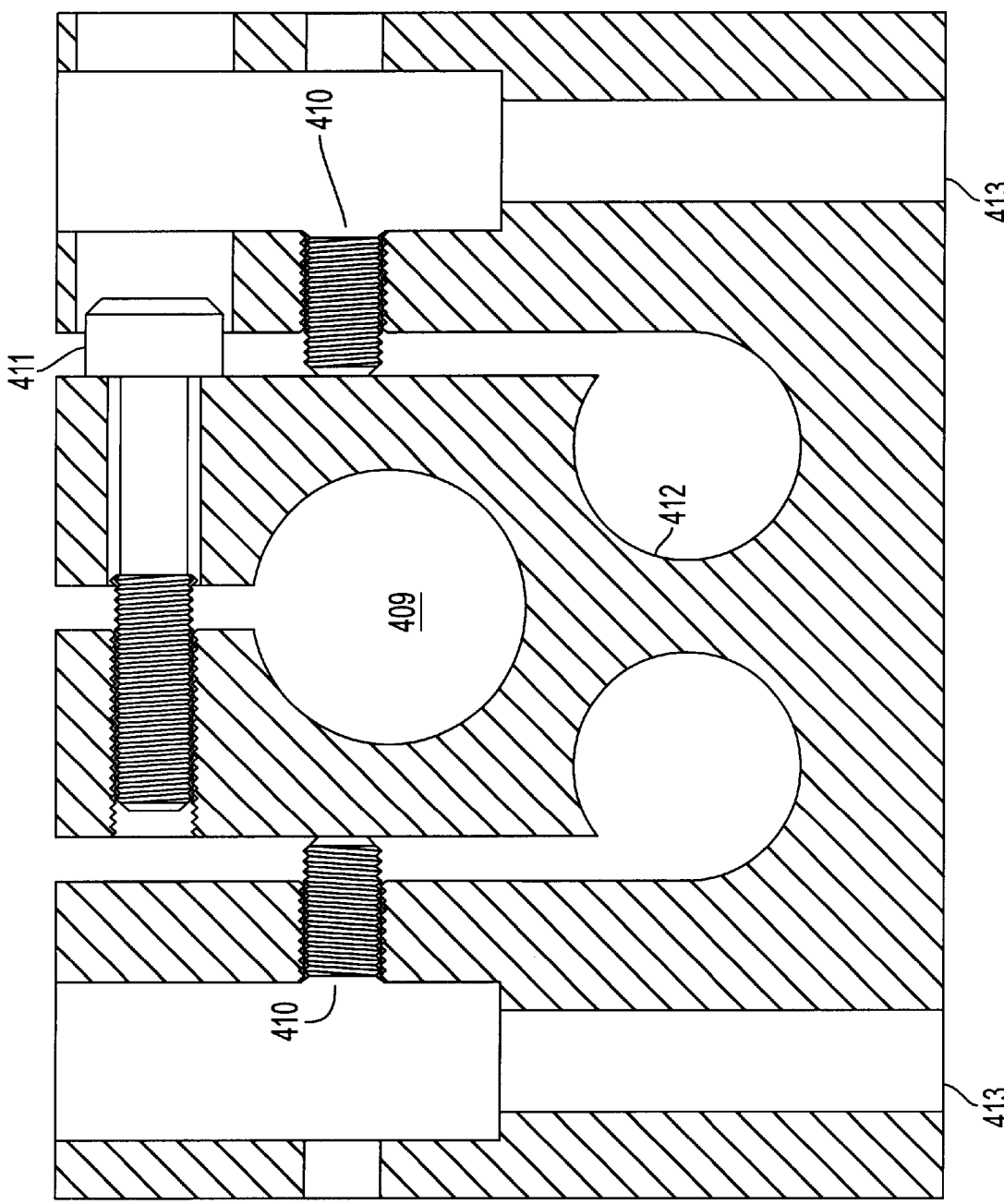

US 6,527,550 B1

APPARATUS AND METHOD FOR PRODUCING A DENTAL PROSTHETIC WITH A DEVICE HAVING A LINEAR ROTARY BEARING

RELATED APPLICATIONS

The present invention is related generally to the subject matter of U.S. Pat. No. 6,190,171 entitled "METHOD AND APPARATUS FOR TOOTH RESTORATION", filed Jul. 21, 1999, which is a U.S. National Phase application of published PCT Application WO98/32392 (corresponding to PCT/US98/00910), and to the subject matter of co-pending U.S. application Ser. No. 09/151,100 entitled "APPARATUS AND METHOD FOR MACHINING A PROSTHETIC TOOTH RESTORATION" filed Sep. 10, 1998, the contents of which are hereby incorporated by reference in their entireties.

BACKGROUND OF THE INVENTION

1. Field of the Invention

The present invention relates generally to the restoration of teeth, and more particularly, to methods and devices for improving the accuracy and simplifying the process of performing such restorations by machining a prosthetic, such as a crown or bridge.

2. Background Information

Numerous methods exist for the restoration of teeth by dentists, including the use of artificial tooth material (such as gold or porcelain) to form a cast-restoration or a metal-ceramic restoration (i.e., dental prosthetics such as crowns). Prosthetic crowns are typically used to repair decayed tooth structure where support from the original tooth structure is either marginal, or unavailable.

Known techniques for preparing a tooth to receive a crown are described in U.S. Pat. No. 5,813,859 in PCT application PCT/US98/00910, both entitled "Method And Apparatus For Tooth Restoration", the contents of which are hereby incorporated by reference in their entireties. As described therein, known techniques of tooth restoration are susceptible to numerous variables, some of which are within the dentist's control and some of which are not. All of these variables can detrimentally influence the accuracy with which: (1) the tooth is prepared to receive the crown; (2) the crown is prepared for placement on the tooth; and (3) the manner by which the crown is fit to and fixed on the prepared tooth.

The quality of a prosthetic crown will vary based on the skill of the person who actually produces the crown (e.g., laboratory technician). More particularly, after the patient's tooth has been shaped to receive the prosthetic crown, an impression is formed from the prepared tooth by placing impression material into the patient's mouth (i.e., to form a negative impression of the prepared and adjacent teeth).

Once the impression has been produced by the dentist, a laboratory technician will set die pins in the impression and then form a master impression as a die (e.g., plaster models) of the patient's teeth. The technician will set the occlusal bite registration and articulate the models of the patient's teeth. Afterwards, the laboratory technician will saw the die to remove the tooth of interest, then trim the die of the tooth and mark the marginal finish line. The sub-structure is then waxed for preparation of the prosthetic crown.

After a wax pattern has been formed, it is converted (i.e., cast or machined) into a sub-structure (e.g., coping) of the crown. It is a challenge to produce a coping that will comply with acceptable tolerances, given the variables associated with the quality of the impression, the skill of the technician and the proper selection of die materials.

For example, U.S. Pat. No. 5,135,393, assigned to Mikrona, describes a coping mechanism for producing parts such as non-metal copings. As described therein, a three-dimensioned pattern is sensed (e.g., traced) with a feeler pin, and then sensed deflections or displacements of the feeler pin are transferred to a motor driven machining tool. As the pattern is traced, the motor driven machining tool operates upon a blank to fabricate a matching three-dimensional coping. The coping is later used by the dental laboratory to build-up a finished crown. That is, once the machined coping has been produced, it is processed with a porcelain build-up. The build-up material incorporates specific shading and color effects to simulate the enamel of the original tooth. The porcelain build-up is then vacuum fired, glazed, polished and fit.

The aforementioned '316 application describes a technique for producing a crown without requiring the need to produce an impression in the manner described above. Rather, the '316 application describes producing a dental prosthetic model of the crown which is to be fit to the patient's prepared tooth. Once the model has been prepared, a dental prosthetic blank, matched in exterior dimensions to the dental prosthetic model is machined so that its interior is matched to that of the model. The entire operation can be performed in the dentist's office, thereby eliminating any need to send an impression to a laboratory technician to produce the dental prosthetic crown.

Prosthetic dental crowns have typically been formed from a combination of metal copings having porcelain formed thereon. Other materials have also been produced and used as dental prosthetic restorations. For example, Ivoclar North America, Inc. of Amherst, N.Y. produces dental prosthetic restorations formed entirely of multi-layered resin composites. Inner layers are formed with fiber structured resin composites to give strength to the overall restoration, and then outer layers are formed of resin composites that can be more easily matched in color and shape to an actual tooth which the restoration is replacing. Due to the wear of the resin composite restorations, Ivoclar has more recently produced crowns formed entirely of ceramic. As referenced herein, "ceramic" materials are those having increased crystalline structure, for example, crystalline structures on the order of 30% or greater. In contrast, "resin" or "resin composite" materials are those which do not possess a crystalline structure in excess of 10%. "Porcelain" materials are those having a crystalline structure on the order of 10% or greater. Definitions of these terms, appear, for example, in the Journal of Dental Research.

The present invention is directed to improving an apparatus for machining a dental prosthetic blank such that it is matched to a dental prosthetic model. In addition, exemplary embodiments are directed to an improved dental prosthetic blank which can be more easily, and more accurately milled to match the dimensions of the dental prosthetic model.

SUMMARY OF THE INVENTION

The present invention is directed to enhancing the accuracy with which tooth restorations are machined, using an apparatus which can accurately copy mill a dental prosthetic blank from a previously formed dental prosthetic model, and which can closely replicate the feel of a dental tool to which dentists are accustomed. In addition, exemplary embodiments are directed to the preparation of a hybrid dental prosthetic blank which can be easily machined.

Exemplary embodiments of the present invention relate to an apparatus for producing a dental prosthetic comprising: means for holding a dental prosthetic model and a dental prosthetic blank having exterior dimensions matched to those of said prosthetic model; and means for machining a three-dimensional surface of said dental prosthetic blank to match a three dimensional surface of said dental prosthetic model, said holding means being rotatable about a single axis, and said machining means having at least one arm mounted for linear rotary motion on a linear rotary axis.

Exemplary embodiments of the present invention also relate to a dental prosthetic blank which can be easily and accurately milled. In accordance with exemplary embodiments, the dental prosthetic blank comprises: a first outer material having at least a 10% crystalline structure for defining an interior cavity and having a first hardness selected as a dental prosthetic material; and a second inner resin material bonded to said interior cavity and having a second hardness, less than said first hardness, selected as a millable material. For example, the dental prosthetic blank includes an outer ceramic material (for example, Empress ™I or II available from Ivoclar) or porcelain, and a second inner material formed of a resin or resin composite (such as Targis™ of Ivoclar). In exemplary embodiments, the blank can be formed using an injection molding process whereby the first outer material is initially formed (for example, injection of a ceramic powder and binder into a die, followed by a sintering process). Afterwards, resin composite material can be injection molded into the outer material.

BRIEF DESCRIPTION OF THE DRAWINGS

Other objects and advantages of the present invention will become more apparent from the following detailed description of the preferred embodiments when read in conjunction with the accompanying drawings, wherein like elements have been designated by like numerals, and wherein:

FIGS. 4A–4C illustrate adjusting means for eliminating radial play between two arms of an upper bearing beam assembly (FIG. 4A) and for adjusting alignment between the upper and lower bearing beam assemblies of the FIG. 1 copy milling apparatus (FIGS. 4B/4C);

DETAILED DESCRIPTION OF THE PREFERRED EMBODIMENTS

1. Overview

Figure 1:
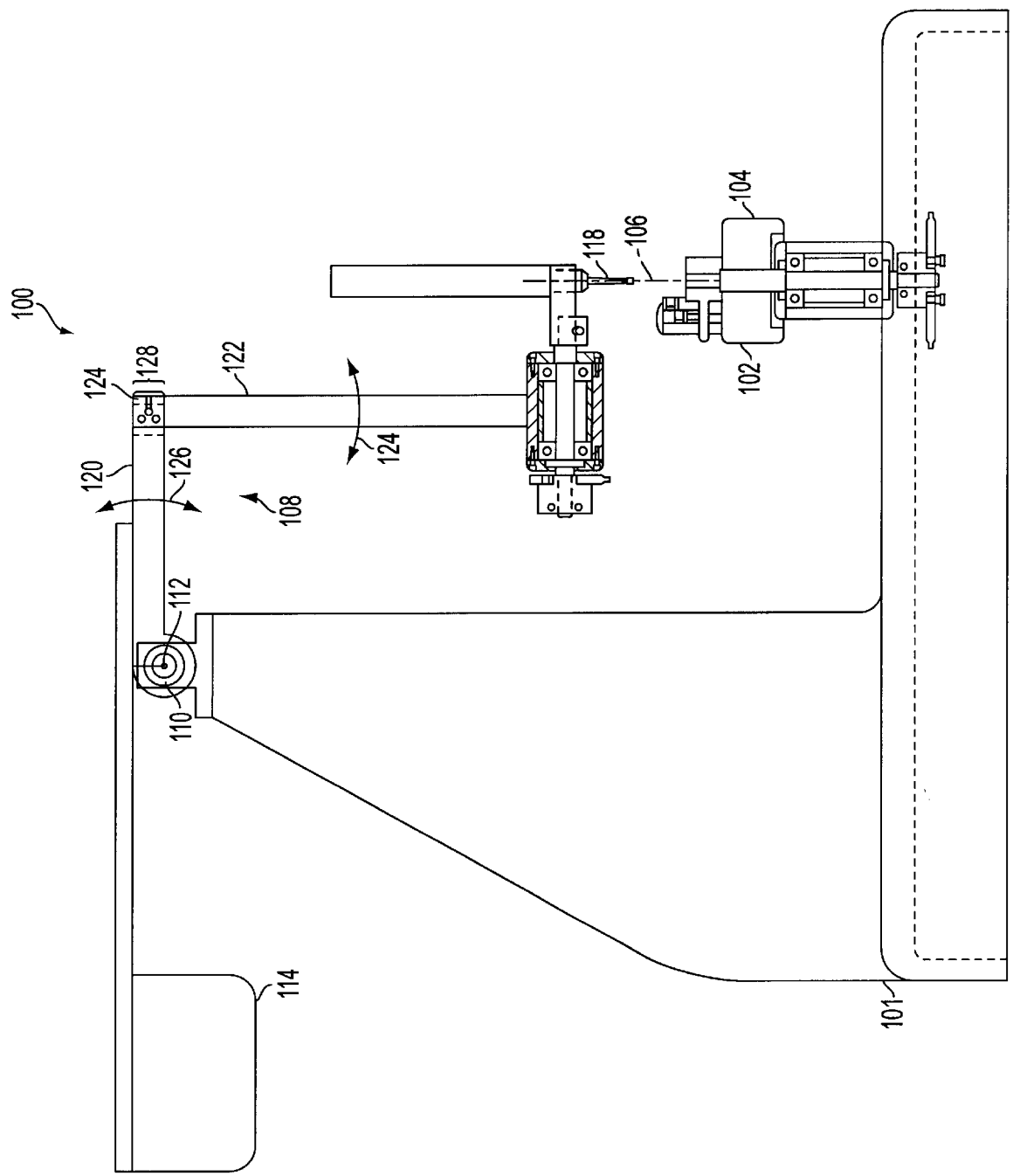
FIG. 1 illustrates a side view of a copy milling apparatus having upper and lower bearing beam assemblies according to an exemplary embodiment of the present invention.

Exemplary embodiments will be described in the context of a prosthetic dental crown (that is, an artificial substitute for the crown of a tooth, including veneers) which can, if desired, be used in conjunction with preparation of a bridge. However, those skilled in the art will appreciate that exemplary embodiments of the present invention can be used to produce any type of finished dental prosthetic, including inlays and onlays.

To prepare a patient's tooth for receiving a dental crown, the tooth is milled by the dentist in conventional manner. A prosthetic model crown is then selected from a series of such prosthetic models, which can be configured in a range of sizes, shapes, shades and types that cover the most common tooth sizes, shapes and shades. The prosthetic models can be substantially prefinished (e.g., seventy percent completed), and can be formed of any material, including any plastic, metal, ceramic, or porcelain material, or can be formed using a hybrid structure as described herein. The range of sizes and types of prosthetic model crowns at the dentist's disposal correspond generally in size and type to a range of prosthetic blanks from which final dental prosthetics can be machined.

The prosthetic model crown is filled with a formable material that allows the dentist to achieve an accurate fit of the prosthetic model crown to the patient's prepared tooth and/or a duplicate model thereof. For example, the prosthetic model crown can be filled with an ultraviolet light curing material, such as the material traditionally used for making dental impressions. The dentist can apply light curing material to an interior of the prosthetic model crown and can allow a portion of the light curing material to protrude from an interior of the prosthetic model crown. The portion of light curing material can be used to fill in the contact area between the shoulder of the prosthetic model crown and the shoulder of the prepared tooth so that an accurate template of the shoulder can be obtained with the light curing material.

Once the prosthetic model crown has been filled with the ultraviolet light curing material, the prosthetic model crown can be pressed over the prepared tooth, and aligned with adjacent teeth. When the dentist is satisfied with placement of the prosthetic model crown over the prepared tooth, the ultraviolet light curing material can be cured (i.e., exposed to ultraviolet light), and any excess material can be trimmed off (e.g., using a dental instrument). Further, exterior sides of the prosthetic model crown can be peripherally milled to adjust contact between the prosthetic model crown and adjacent teeth. Top surfaces of the prosthetic model crown can also be spot milled as necessary to achieve more exact occlusion.

The prosthetic model crown is next removed from the prepared tooth for use as a template in milling a prosthetic blank to produce a final prosthetic dental crown. In accordance with exemplary embodiments, the final prosthetic dental crown is produced by milling a prosthetic blank which has exterior dimensions matched to those of the prosthetic model.

2. Copy Milling Apparatus

Because the prosthetic model crown has been formed as a template representing a desired fit of the prosthetic model crown to the prepared tooth, the prosthetic blank is milled to match the prosthetic model crown. An exemplary apparatus for matching a prosthetic blank to the prosthetic model crown includes a means for machining the prosthetic model crown. A holding means is provided for holding the dental prosthetic model crown and the dental prosthetic blank.

Figure 3:
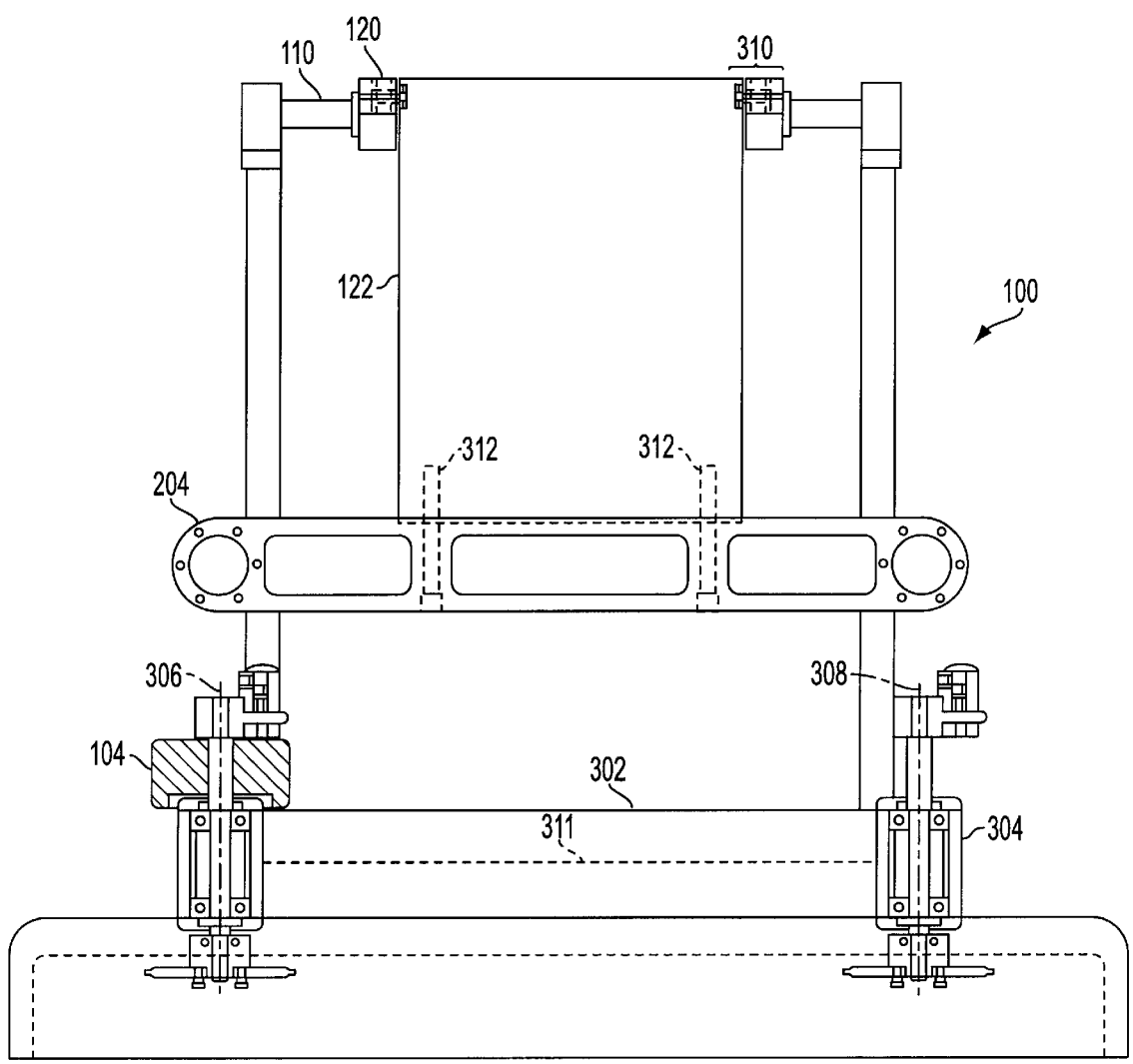
FIG. 3 shows a partial front view of the FIG. 1 copy milling apparatus.

A side view of an exemplary copy milling apparatus 100 configured in accordance with the present invention is shown in FIG. 1 to include means for holding a dental prosthetic model and a dental prosthetic blank having exterior dimensions matched to those of the prosthetic model. The holding means includes a lower bearing beam assembly 102. Because FIG. 1 is a side view, only the portion of the holding means used to fix a dental prosthetic model is illustrated. The holding fixture 104 is represented as a first holding fixture 104 rotatable about a first axis 106. A second holding fixture for holding dental prosthetic blank to be milled so that its dimensions match those of the dental prosthetic model is illustrated in FIG. 3 as a second holding fixture 304.

Referring to FIG. 1, a means for machining a surface of the dental prosthetic blank to match a surface of the dental prosthetic model is illustrated as including an upper beam assembly 108. The upper beam assembly is supported an upper arm 120 mounted to a linear rotary bearing 110 having a bearing rail which passes through a bearing that permits the entire upper beam assembly 108 to slide in a lateral direction (i.e., into and out of the FIG. 1 drawing in a direction perpendicular to the page), and to rotate about an axis 112 such that the entire milling tool can be pivoted upward and downward in a direction of arrow 126. The rotary linear bearing used in accordance with the exemplary embodiments can be any such bearing which permits linear motion and rotation with respect to a common axis. Such bearings are readily available including, but not limited to, the Miniature Stroke Rotary Bushing series parts used for providing rotary/linear motion, available from Iko Corp. of Japan. To provide a sense of feel to the dentist, a counterforce configured as a spring or as a counterweight 114 is provided to stabilize the milling tool about rotary axis 112.

Figure 2:
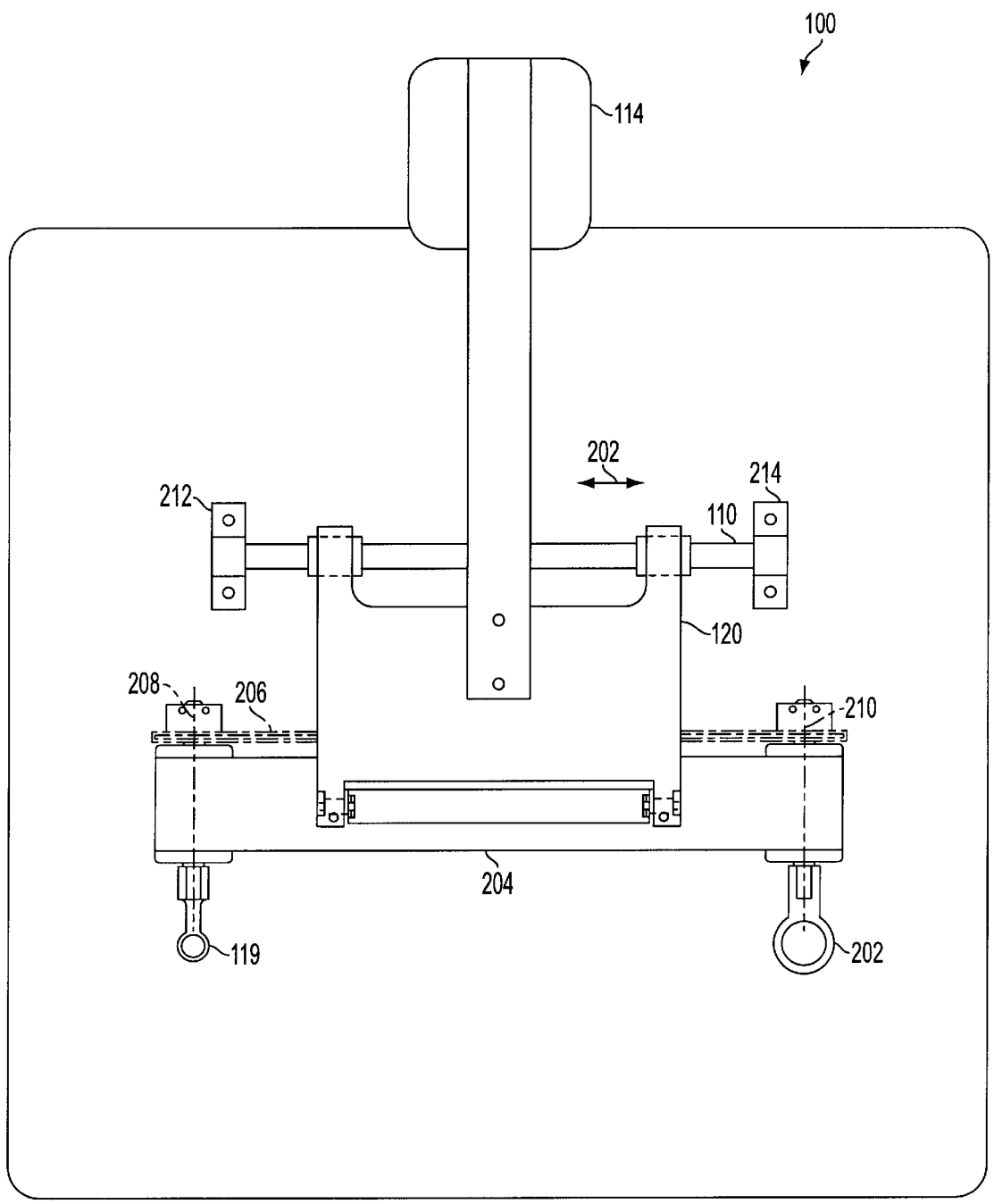
FIG. 2 illustrates a top view of the FIG. 1 upper beam assembly and its support.

Because FIG. 1 is a side view, only a tracing stylus 118 can be viewed. However, a quick reference to FIG. 2 illustrates that in addition to the tracing stylus accommodated in a tracing stylus mount 119 and used to trace the dental prosthetic model, a parallel cutting tool mount 202, which can be seen from the top view of FIG. 2, is provided for receiving a cutting tool. The cutting tool mimics the movements of the tracing stylus to mill the dental prosthetic blank to match dimensions of the dental prosthetic model. Those skilled in the art will appreciate that any conventional cutting tool appropriately sized to fit in the tool mount 202 can be used, with the cutting tip material (e.g., diamond tipped) being selected as a function of the material to be milled.

Referring to FIG. 1, in addition to being linearly movable and pivotally rotatable with respect to the axis 112, the tracing stylus and cutting tool of the copy milling apparatus can include another arm 122 pivotably connected to arm 120 for rotation about an axis 124. This permits movement of the tracing stylus and tool in the direction of arrow 124 about axis 124. The arms 120 and 122 can be formed as a rocker plate and a suspension plate, respectively.

FIG. 2 shows a top view of the FIG. 1 copy milling apparatus 100, and better illustrates how the first arm 120, and thus the entire upper bearing beam assembly 108, is slidable along the linear rotary bearing 110 in a direction 202, and rotatable about axis 112. The second arm 122 is pivotally mounted to the first arm 120 in FIG. 2. The tracing stylus mount 119 can be seen to the left hand side of FIG. 2, and the cutting tool mount 202 can be seen to the right hand side of a bearing beam 204 used to operably connect movements of the tracing stylus 118 with movements of the cutting tool. Interconnected movements of the tracing stylus and the cutting tool can be achieved in a fashion as described in the co-pending U.S. application Ser. No. 09/151,100, the disclosure of which is incorporated herein by reference. The tracing stylus and the tool, in addition to being linked via the beam 204, are rotationally connected via a linkage 206 (e.g., a linked chain, or other coupling), such that rotations of the tracing stylus about an axis 208, will be translated into rotations of the cutting tool about a parallel axis 210.

FIG. 3 shows a front view of the FIG. 1 copy milling apparatus 100, wherein the second arm 122, which was vertically oriented in FIG. 2, can now be better seen. For purposes of simplifying the illustration, the tracing stylus and the tool are not shown mounted to the bearing beam 204 in FIG. 3. When mounted, the stylus and tool would be fixed in stylus and tool holders attached to the bearing beam 204, in vertical alignment with holding fixtures of a lower beam assembly 302. The bearing beam 204 is mounted to the arm 122 via attaching screws, such as screws 312. The first arm 120, which supports the second arm 122, is movable about the rotary linear bearing 110 shown at the upper portion of FIG. 3.

In FIG. 3, although the tracing stylus and cutting tool have been removed from the beam 204, the first holding fixture 104 and the second holding fixture 304 for retaining the dental prosthetic model and blank, respectfully, can be seen on the lower beam assembly 302. Each of these holding fixtures is rotatable about a single axis. That is, holding fixture 104 is rotatable about an axis 306, and the dental prosthetic blank holding fixture 304 is rotatable about a second, parallel axis 308. A linkage, similar to that described in conjunction with the holding fixtures of the co-pending U.S. application Ser. No. 09/151,100 can be used to translate rotations of the dental prosthetic blank holding fixture 104 into rotational movement of the dental prosthetic blank holding fixture 304. For example, a linkage represented by its centerline 311 can be included to drive rotations of the holding fixture 304 in response to rotations of the holding fixture 104.

As those skilled in the art will appreciate, it is important to maintain a high degree of precision during assembly of the apparatus. That is, the tracing stylus and the tool must be aligned with respect to the holding fixtures 104 and 204 such that movements of the tracing stylus relative to a dental prosthetic model can be accurately replicated by the tool with respect to the second holding fixture 304 during a milling operation. Accordingly, the same materials can be used to implement the upper and lower beam assemblies of the copy milling apparatus 100 to avoid competing coefficients of thermal expansion from altering alignment. The material used for the exemplary apparatus can be steel, aluminum, or any other material which can achieve the desired rigidity, and provide alignment within the desired tolerance.

Center distances between spindles on each of the upper and lower beams should be held very precisely. Exemplary embodiments use a single piece spindle beam for holding the tracing stylus and cutting tool (i.e., the beam 204). Similarly, a single beam 302 is used to fix each of the first and second holding fixtures. As such, center distance variation due to assembly tolerance variation is eliminated, even when the copy milling apparatus is subjected to shock or other abuse. The use of a single rigid beam for each of the upper and lower beam assemblies also reduces overall parts count and simplifies the overall assembly process. The use of pivoting members, such as the arms 120 and 122 also reduces the part count and simplifies the assembly process. Further, such an implementation is less susceptible to contamination from dust and dirt, and produces less drag to provide a smoother movement of the stylus. The use of a configuration having only a single linear axis of movement renders it easier to seal off a machining side of the copy milling apparatus, to remove dust and debris, and to provide liquid coolant.

In accordance with exemplary embodiments, optional adjustments can be included at any of various locations in the copy milling apparatus 100 to fine tune alignment.

Figure 4A:
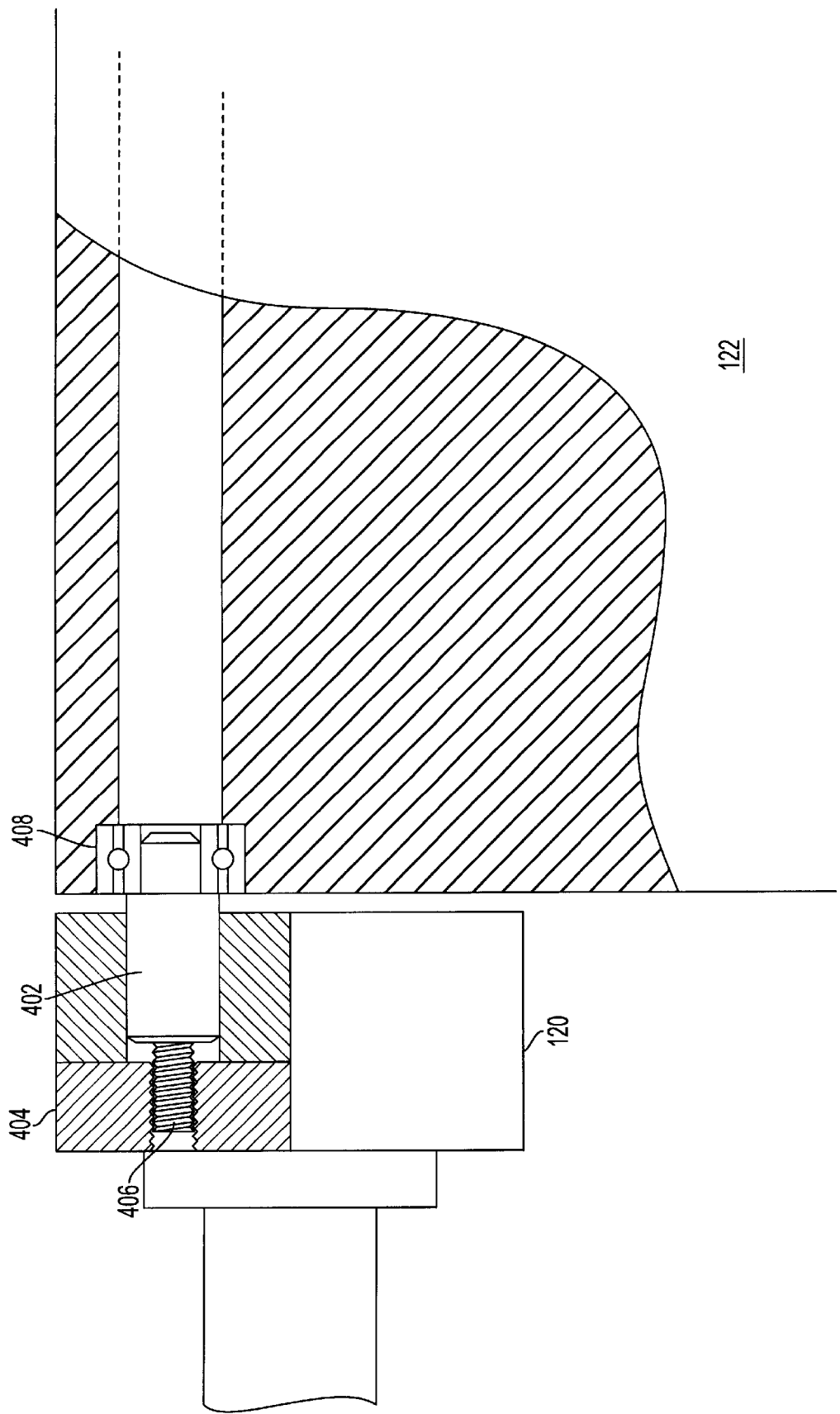

Referring to FIG. 4A, an exemplary adjustment means associated with the FIG. 1 upper bearing beam assembly is illustrated in greater detail. The adjustment means of FIG. 4A is provided at one end of the pivotal connection of arm 122 to arm 120. Those skilled in the art will appreciate that the other side of arm 122 can be pivotally connected to arm 120 in similar fashion. A portion of arm 122 is shown in partial cross-section to better illustrate this adjustment.

The adjustment 128 includes two pivot pins 402 (one at each end of arm 122) mounted in clamping holders 404 located on the ends of the upper arm 120, with set screws 406 backing up the pins. As shown, each of the pins are formed with a first large diameter portion for placement in the clamp holder 404, and a second small diameter portion for placement in the race of the pivot bearing 408. By adjusting the set screws the pivot pins are movable axially together, thereby causing a preload condition between the inner and outer races of pivot bearings 408. This preload removes axial and radial play from the pivot system formed by the pivot bearing, which if present, could cause copy milling errors. When proper preload is achieved, the pivot pins are firmly located in place by means of clamping screws (not shown), such that the entire upper bearing beam assembly will operate as a unit that can be finely aligned with the lower bearing beam assembly in a manner to be described with respect to FIGS. 4B and 4C.

Because machining tolerance variations on the parts comprising the assembly could cause misalignment of the upper bearing beam of the copy milling apparatus 100 with respect to the lower bearing beam assembly, copy milling errors can result on the dental prosthetic blank. Accordingly, a horizontally adjustable mount is optionally provided on one end of the bearing rail of the linear rotary bearing 110 upon which the upper arm 120 slides/pivots, and a vertically adjustable mount is provided on the other end. Such a feature makes it possible to fine tune alignment in the horizontal and vertical planes, and provides the opportunity to compensate for misalignments due to wear, shock, or other abuse.

FIG. 4B shows an adjustment mechanism which can be mounted to the FIG. 1 base structure 101 to correct lateral misalignments of the upper bearing beam assembly with respect to the lower bearing beam assembly. For example, the FIG. 4B adjustment can be included at one end of the linear rotary bearing 110, and used to mount the bearing rail to the base structure of FIG. 1. The FIG. 4B adjustment can be mounted to the base structure 101 of the FIG. 1 apparatus via screws inserted into mounting holes 413. The adjustment is provided with a bore 409 through which the bearing rail of the linear rotary bearing 110 passes. A clamping screw 411 can be used to adjust the pressure with which the bearing rail is fastened.

The adjustment also includes set screws 410 and a thin beam section 412, which can be deflected by the set screws to laterally offset the upper bearing beam 204 relative to the lower bearing beam. Lateral adjustment can be achieved by adjusting the set screws 410 to the desired offset, and then tightening the clamping screw 411 to lock the bearing rail into the mount.

Figure 4C:
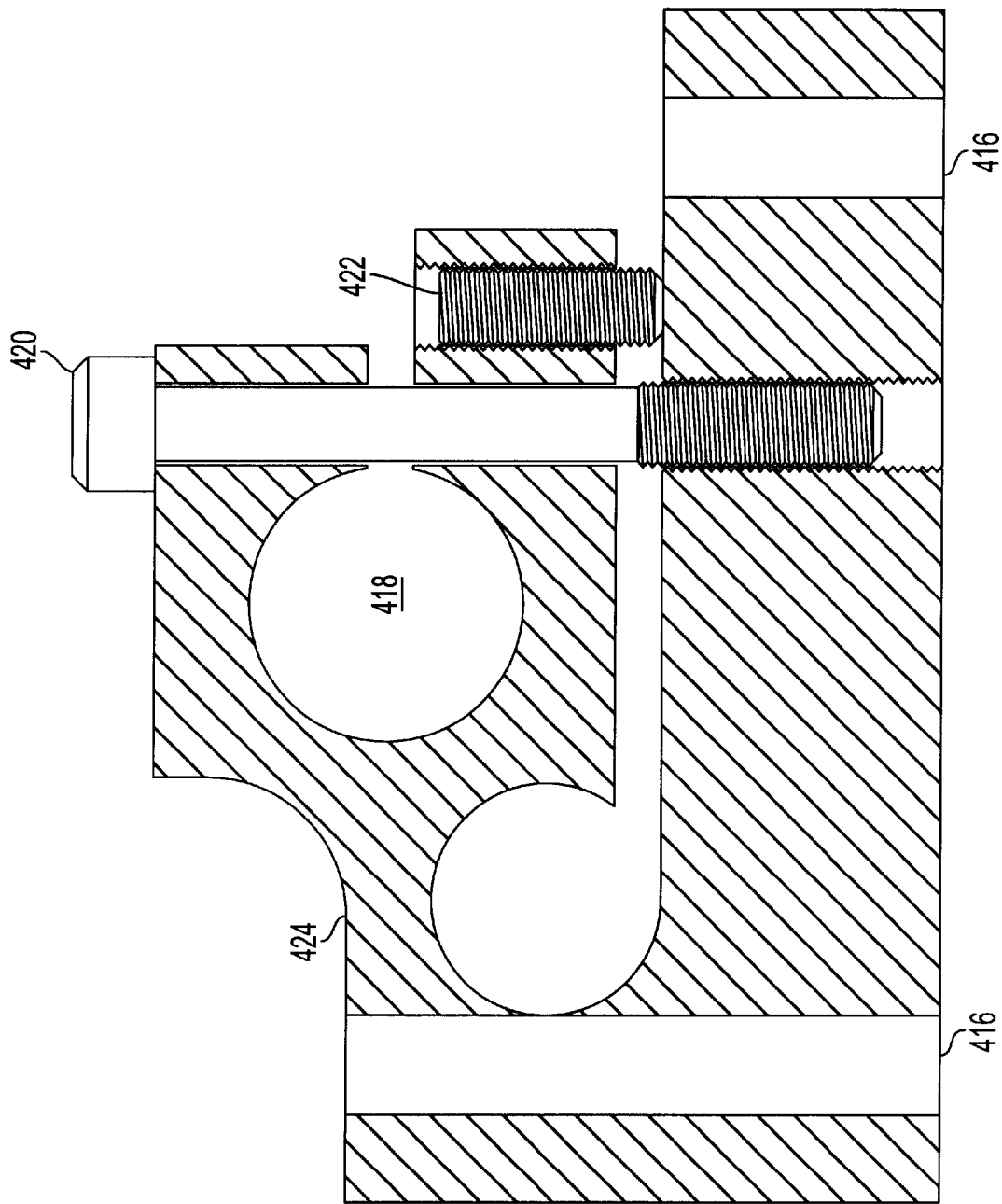

FIG. 4C illustrates an adjustment mechanism which can be used to align the orientation of the upper bearing beam relative to the lower bearing beam in a vertical direction. The FIG. 4C adjustment can be mounted to the base structure 101 at an end of the bearing rail of the linear rotary bearing which is opposite the end where the FIG. 4B adjustment is mounted. The FIG. 4C adjustment can be mounted to the base structure using screws supplied through mounting holes 416. Again, a bore 418 is provided through which the bearing rail of the linear rotary bearing passes. A clamping screw 420 can be used to adjust the pressure with which the bearing rail is fastened within the FIG. 4C adjustment.

The FIG. 4C adjustment includes a set screw 422 and a thin beam section 424 which can be deflected by the set screw to vertically offset the upper bearing beam assembly relative to the lower bearing beam. Vertical adjustment is achieved by adjusting the set screw 422 to bring the bearing rail which passes through the bore 418 to the proper height, and then tightening the clamp screw 420 to lock the bearing rail into the mount and to pull a rail clamp section of the FIG. 4C adjustment down tightly against the set screw.

The adjustments of FIGS. 4B and 4C can, for example, be used as the bearing rail mounts 212 and 214, respectively of FIG. 2. In an exemplary embodiment, the upper arm 120 can be loosely mounted, using the linear rotary bearing 110, within the mounts 212 and 214. The FIG. 4A adjustment can then be used to fine tune the connection of the lower arm 122 to the upper arm 120. Afterwards, the FIGS. 4B and 4C adjustments can be used to fine tune the alignment of the upper bearing beam assembly to the lower bearing beam assembly.

Those skilled in the art will appreciate that any of adjusting mechanisms described can be placed at any location in the FIG. 1 copy milling apparatus deemed suitable to achieve a desired alignment, and that any other desired adjustments can be added.

Those skilled in the art will appreciate that the various spindles (i.e., the stylus/cutting tool spindles, and the tool fixture spindles) can be coupled together using, for example, a chain and gear assembly. Spring compression (e.g., coil springs) can be used to establish tension, and remove backlash from spindle rotation. As those skilled in the art will appreciate, the rotation need only be 180° in the upper beam assembly to achieve satisfactory range of motion. The desire is to decrease the weight of the upper bearing beam because this portion is cantilevered using the first and second arms 120, 122. Accordingly, the upper beam used to hold the stylus and cutting tool can be hollow, and can include spindle rotation of only 180° to minimize weight. In contrast, the spindles in the lower beam assembly can be permitted to rotate a full 360°.

In operation, the prosthetic model crown is placed into the holding means. The holding fixtures, or holders, can be symmetrically configured to allow placement of the prosthetic model crown and prosthetic blank in either an upright or an upside-down orientation. The prosthetic model crown can, for example, be initially placed upside down in the first holding fixture so that the surface formed with the cured ultraviolet light curing material is readily accessible by a tracing stylus and then inverted for exterior milling.

Clamps can be provided in each of the first and second holding fixtures. Locations of the clamps are matched to registration marks of the prosthetic model crown and the prosthetic blank, respectively. In an exemplary embodiment, adjustable means are provided to allow the prosthetic model crown to be inserted into the holding fixture, and then retained in place. For example, an adjusting screw can be provided to apply pressure to an exterior of the prosthetic model crown via the clamps, to thereby fix the prosthetic model crown in place.

The dental prosthetic model crown is placed in the first holding fixture can be manually rotated about an axis of the left hand spindle, while the dental prosthetic blank to be milled is placed in the second, similar holding fixture on a parallel right hand spindle that rotates about a parallel axis of the right hand spindle. The left and right hand spindles are rotationally connected to each other by the synchronized drive means, such as a chain or belt drivingly connected with gears that are fixed to respective spindles of first and second fixtures. Thus, any rotary motion imparted by the machine operator to the dental prosthetic model crown in the first holding fixture can be duplicated by the second hold fixture with respect to the dental prosthetic blank to be milled. The cutting tool can, of course, be any milling device, such as diamond burs used as conventional dental tools.

As those skilled in the art will appreciate, any number of registration marks can be included on the prosthetic model crown to hold it in place within the holding fixture. As was the case with the prosthetic model crown, the prosthetic blank can be held in place via clamps and an adjusting screw.

In accordance with exemplary embodiments, the prosthetic crown blank can include finished exterior surfaces, with the exception of the surface that is to mate with the prepared tooth. Due to the use of the registration marks and clamps being in identical positions in the prosthetic model crown and on the prosthetic blank, a tracing of the prosthetic model crown as a template can be used to match an interior of the prosthetic blank to the shape of the prepared tooth.

For this purpose, the stylus can be traced over the prosthetic model crown, with motions of the stylus being used to control movement of the cutting tool over a surface of the prosthetic blank. Because the registration marks are used to locate the prosthetic model crown and the prosthetic blank in exactly the same orientation, exact alignment of outside contours between the prosthetic model crown and the prosthetic blank can be assured, such that exact machining of the prosthetic blank interior can be achieved. Such machining can be performed in known fashion, such as in the manner described in the aforementioned U.S. Pat. No. 5,135,393, the contents of which are hereby incorporated by reference in their entirety.

The tracing stylus is mounted to a "C" rotary axis spindle on the left hand side (as viewed) in FIG. 3 and the motorized cutting tool having a shape matched to that of the stylus is mounted to a parallel "C" rotary axis spindle on the right hand side of FIG. 3. The left and right hand parallel "C" axis spindles are rotationally connected to each other by a synchronized drive means, such as a chain or belt 321 drivingly connected with gears that are fixed to respective "C" axis spindles. Thus, any rotary motion imparted by the machine operator to the tracing stylus is exactly duplicated by the cutting tool.

In accordance with exemplary embodiments, the counterweight 114 offsets the weight of the stylus, cutting tool and cutting tool motor. As such, rotations of the stylus and cutting tool about the "C" axis can be maintained in any position when the machine operator releases the stylus. Of course, those skilled in the art will appreciate that any mechanism for providing the counterweight features described can be used, such as any appropriately sized metal weights or spring biases or any other counterweight measure. Similarly, counterweights can be provided in any arrangement desired, which will ensure that the stylus and cutter remain motionless when the operator refrains from any motion thereof.

Once an interior (i.e., tooth mating surface) of the prosthetic blank has been achieved, exterior surfaces of the prosthetic model crown can be traced and used to achieve similar milling of an exterior of the prosthetic blank crown. That is, peripheral side surfaces and the top surface of the prosthetic crown can be spot milled.

In accordance with exemplary embodiments, the first and second holding fixtures for holding the dental prosthetic model and the dental prosthetic crown can be configured with symmetrical cavities. As such, the dental prosthetic model and the dental prosthetic blank can be placed into their respective fixtures in either the upright or in an inverted position so that all sides of the dental prosthetic model and the dental prosthetic blank can be accessed by the stylus and cutting tool. For example, the use of a T-shaped tang as will be discussed with respect to FIG. 5 can be used to permit inversion of the dental prosthetic model and/or dental prosthetic blank in their respective holding fixtures.

After all machining of the prosthetic blank has been completed, both the prosthetic model crown and the prosthetic blank can be removed from the holding fixtures. Locating features included on the prosthetic blank can then be ground or polished off or, in the case where they are formed as recesses, can be filled. Because all exterior surfaces of the prosthetic blank will be formed as finished surfaces, the prosthetic blank now constitutes a finished crown which requires no porcelain build-up or sintering, but which can be immediately bonded into place over the prepared tooth of the patient.

Of course, exemplary embodiments are not limited to the preparation of a prosthetic dental crown, and can be used for any dental prosthetic including but not limited to any tooth veneer, or any dental bridge. For example, the multiple prosthetic model crowns used to form a bridge template can be traced in order to machine a single prosthetic blank formed large enough to serve as a bridge. In this case, the entire bridge is machined as a single piece from a template.

Those skilled in the art will appreciate that exemplary embodiments of the present invention can also be used to machine prosthetic blanks into prosthetic inlays and onlays. For example, an impression material can be placed into the inlay or onlay area of the patient's tooth, and a prefabricated prosthetic can be placed in the impression material. The impression material can then be cured and any excess impression material removed to provide a template of the inlay or onlay. Afterwards, a machining of a blank inlay or onlay can be performed using the prepared template in the manner described previously with respect to the prosthetic crown.

Of course, those skilled in the art will appreciate that alternate embodiments of the present invention exist. For example, the FIG. 3 apparatus can be configured with adjustments to accommodate any size prosthetic model and/or prosthetic blank, or alternately, a separate apparatus can be configured for different types of teeth (e.g., one size for molars, one size for bicuspids and so forth).

4. Dental Prosthetic Blanks

The prosthetic blanks can be produced from materials used to produce conventional dental crowns. For example, a first exterior material, such as porcelain or ceramic can be built up on a second interior material such as a gold coping. The interior material of the prosthetic blank can then be milled to match the prosthetic model. The use of the metal interior in the prosthetic blank allows the finished prosthetic to be cemented into place on the prepared tooth of a patient.

In accordance with other embodiments, the prosthetic blank can be formed of a single material, such as porcelain or ceramic, and milled in accordance with exemplary embodiments of the present invention. Afterwards, the prepared interior of the prosthetic blank can be milled a predetermined amount (e.g., approximately 0.2 mm), to accommodate a coating of the interior with a second material more suitable for cementing the prosthetic to the prepared tooth of a patient. For example, a second material, such as metal (e.g., gold) can be applied to the milled interior of the prosthetic through, for example, electroplating.

In accordance with yet other embodiments, a dental prosthetic can be formed as a hybrid. The hybrid blank can be formed with a first material as an outer layer (e.g., a high strength ceramic material, which is wear resistant and strong), and with a second material used to form an inner layer (e.g., a softer material which is easily machinable, including but not limited to, a resin composite material). The second material is bonded to an interior cavity of the outer layer. The outer material can be injection molded (e.g., injection of ceramic powder and binder into a die, followed by a sintering process), and then the softer inner material can be bonded (e.g., injection molded) to the interior cavity thereof. For example, an inner layer of resin can be bonded by internally etching an outer ceramic material with hydrofluoric acid and applying a layer of saline for chemical enhancement of a bond to the component resin. Alternately, the outer layer can be fabricated as a ceramic shell, and a softer, machinable ceramic can be sintered as the inner layer. As those skilled in the art will appreciate, the first and second materials should be matched in terms of their coefficient of thermal expansion to avoid cracking of the ceramics.

Figure 5A:
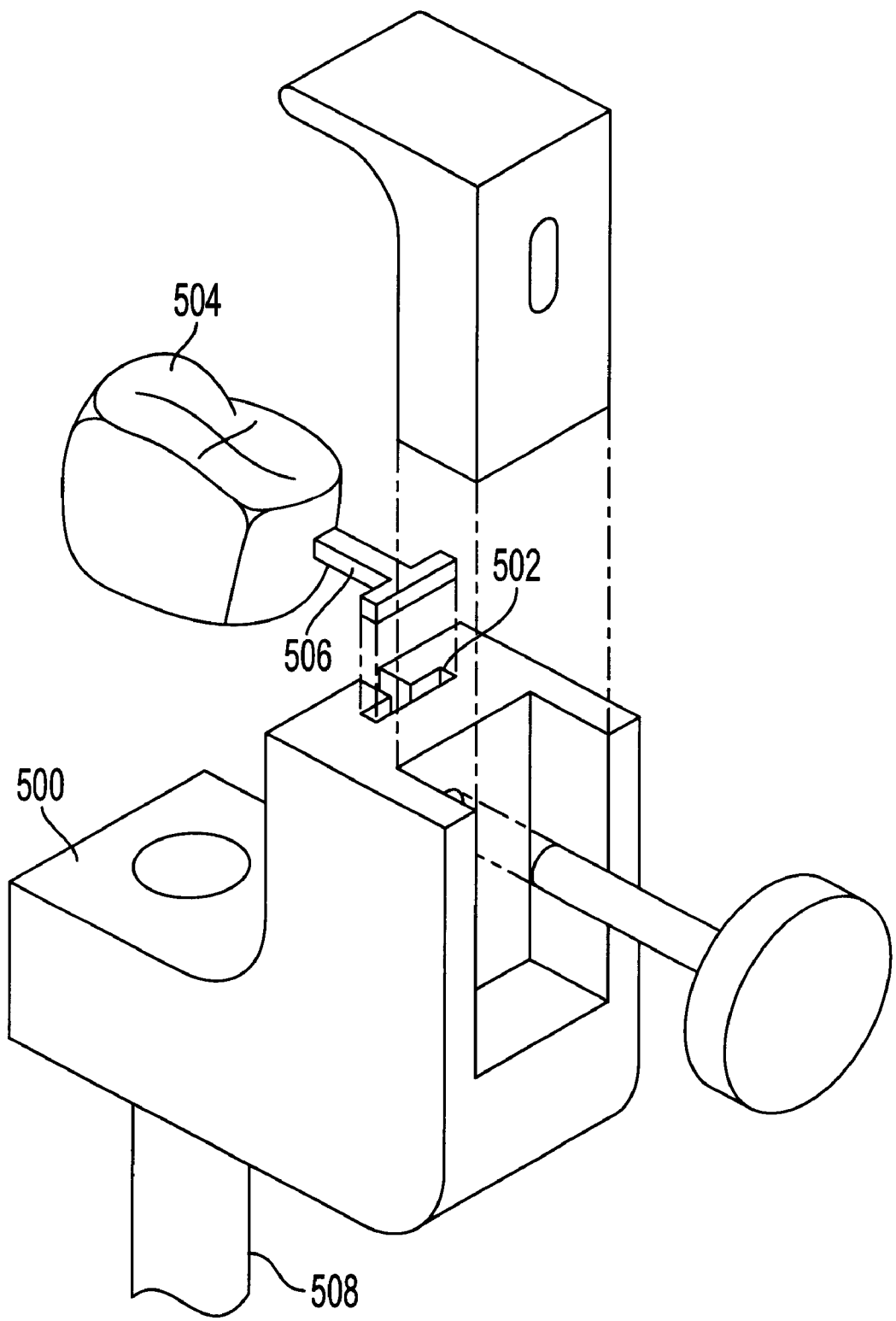
FIGS. 5A–5C illustrate an exemplary embodiment of a holder which can be used in accordance with the FIG. 1 embodiment.
Figure 5B:
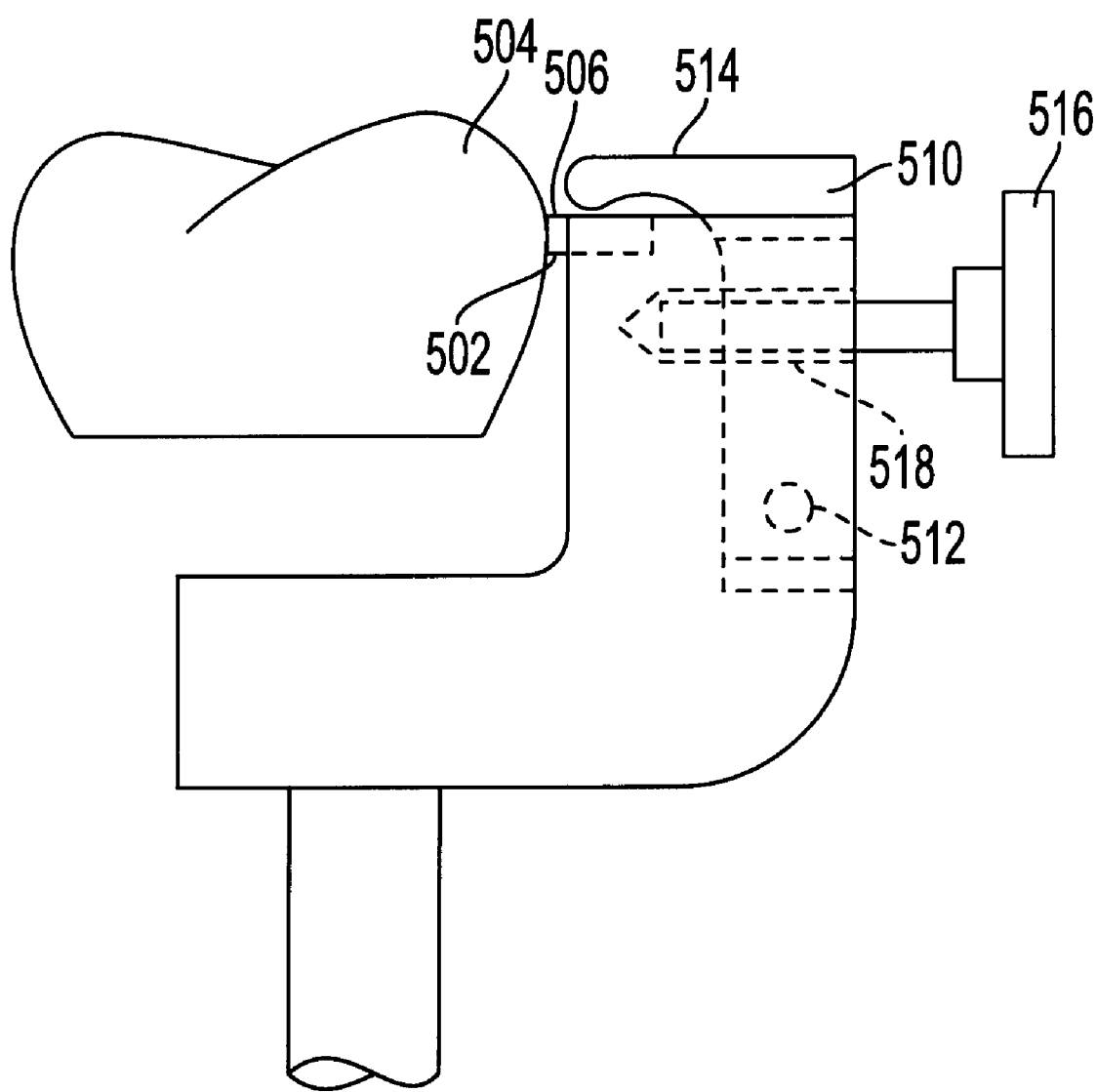
Figure 5C:
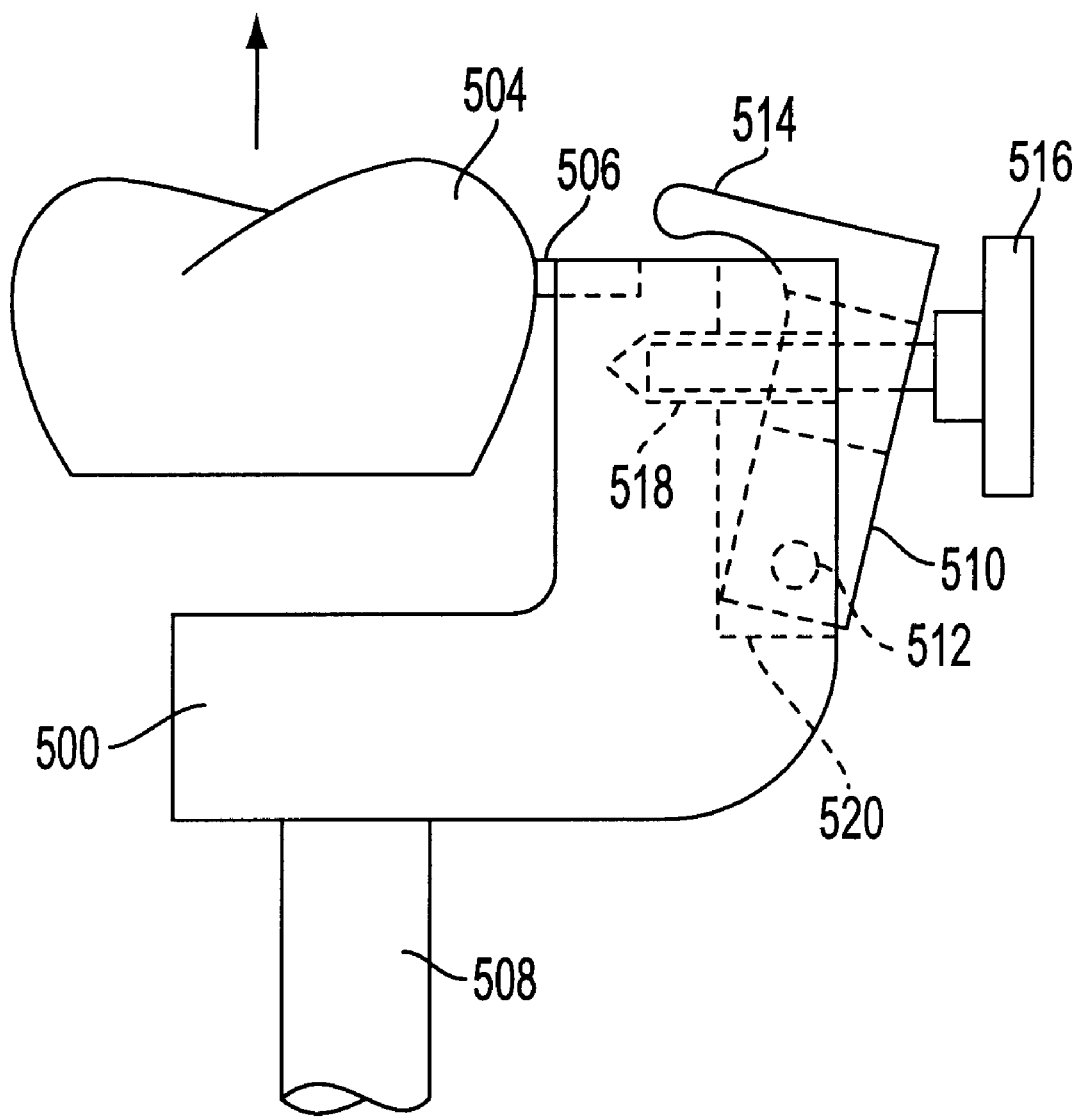

FIGS. 5A–5C illustrate an exemplary prosthetic blank and/or prosthetic model crown, as well as a holding means which can be used in conjunction with the milling apparatus of FIG. 3. In FIG. 5A, a removable fixture 500 is provided, which can be mounted to each of the "B" axis spindles in the FIG. 3 apparatus, and which has a general "L" shape in the FIG. 5 embodiment. The fixture 500 includes a nested opening 502 which can be used to positively locate a prosthetic blank and/or a prosthetic model crown. The prosthetic blank and/or prosthetic model crown 504 can be configured, as illustrated in FIG. 5A. As illustrated therein, a registration mark is formed as a "T" shaped tang molded onto the periphery of the blank and/or crown as a male connector which can be mated to the nested opening 502 to positively register the blank/crown with the fixture 500. Of course, those skilled in the art will appreciate that the tang can be configured in any acceptable manner, provided a suitable mating can be achieved with respect to the fixture 500.

The fixture 500 can be removably mounted into the FIG. 3 apparatus, via a rotatable shaft 508 which can be clamped into the FIG. 3 apparatus in a corresponding receptacle of the first or second holding fixture. Of course, similar fixtures 500 can be associated with either or both of the holding fixtures used in the FIG. 3 apparatus for the prosthetic blank and/or the prosthetic model crown.

FIG. 5B illustrates the mechanism which can be included with the locating fixture 500 to clamp the prosthetic blank or prosthetic model crown into the fixture. As illustrated in FIG. 5B, after the "T" shaped tang 506 has been inserted into the nested opening 502, a clamping mechanism 510, which is pivotable about a pivot 512, can be displaced such that a clamping tip 514 is located over the "T" shaped tang 506. A thumb screw 516 can then be used to lock the clamp 510 into place by, for example, rotating in a clockwise direction such that a screw 518 which passes through the clamp 510 can lock the clamp in a closed position.

FIG. 5C illustrates the clamp 510 in an open position. As illustrated in FIG. 5C, the thumb screw 516 has been rotated in a reverse, counterclockwise direction, thereby permitting the clamp 510 to be pivoted about axis 512 away from a position where the clamping tip 514 engages the "T" shaped tang 506. As such, the prosthetic blank and/or prosthetic model crown can be removed vertically from the fixture 500. As illustrated in FIG. 5C, the clamp 510 moves about the axis 512 within an opening 520 of the fixture 500.

In accordance with exemplary embodiments, the "T" shaped tang 506 can be formed of any suitable material. For example, the "T" shaped tang 506 can be configured of the same material used to produce the prosthetic blank and/or prosthetic model crown. After the prosthetic model crown has been prepared, it can be removed from the fixture 500 and then the "T" shaped tang can be removed therefrom (e.g., milled in the same way that the elements 204 of FIG. 2A are removed) and polished.

Referring to FIGS. 6A–6E, an alternate embodiment of a holder which can be used in conjunction with the FIG. 3 apparatus is illustrated. The holder can accurately locate and hold a dental prosthetic blank or prosthetic model. The exemplary holder illustrated provides a repeatable, accurate locating of a registration feature, such as a tang, which is configured as a part of the dental prosthetic or prosthetic model. In addition, the holder as illustrated provides automatic ejection of the tang when the holder is opened. A clamping device is provided which automatically rotates into position when tightening the holder, and rotates out of the way (e.g., 90° out of the way) when the holder is loosened. As such, the operator has a clear view of the cavity into which the tang is placed, and the holder can be operated using one hand, leaving the other hand free to hold and position the tang within the holding device.

Figure 6C:
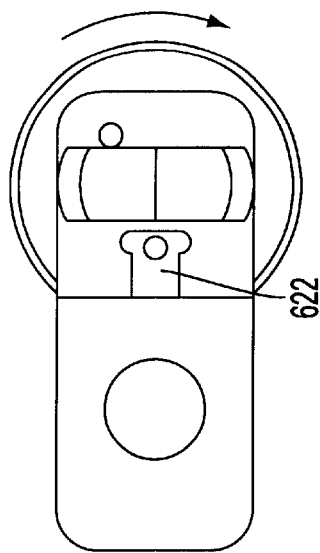
FIGS. 6A–6E illustrate additional features of the holder.
Figure 6D:
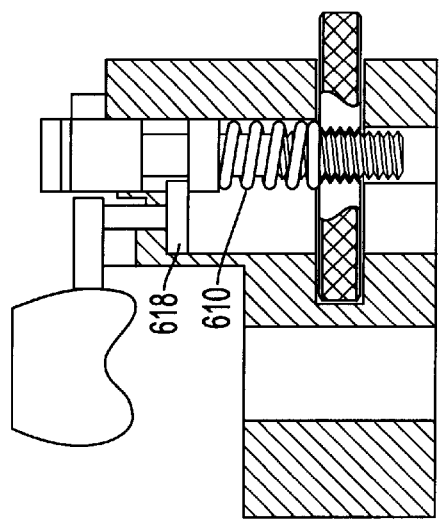
Figure 6A:
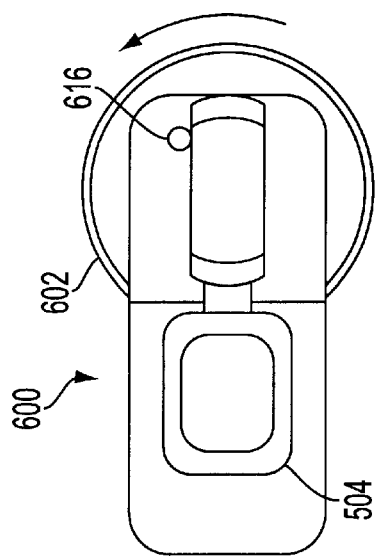
Figure 6B:
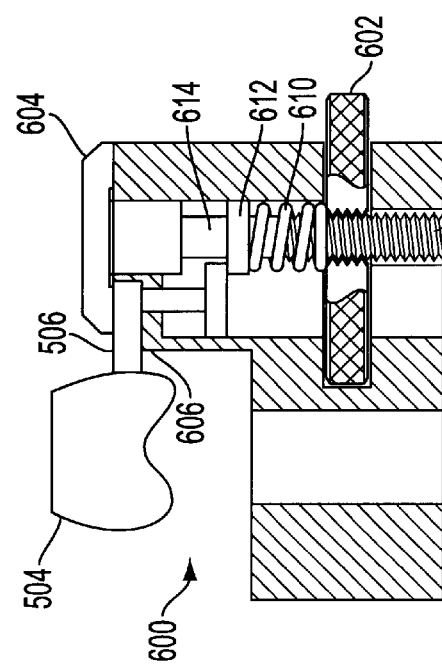

FIG. 6A illustrates a holder in a closed position. The FIG. 6A holder is designated 600, and includes a rotatable, knurled knob 602. The knob 602 can be rotated in a counterclockwise direction to close the holder, and rotated in a clockwise direction to open the holder or vice verse. As shown in FIG. 6B, the "T" shaped tang 506 of FIG. 5 is located between a clamp 604 and an upper surface 606 of a "T" shaped recess 622 in the holder 600. In FIG. 6B, the clamping device has been rotated over and pulled down upon the tang 506 by rotation of the knob 602 about a threaded shaft 608.

The operator places a dental prosthetic blank or prosthetic model crown with a tang above the cavity, and then rotates the knurled knob 602 counterclockwise. Upon rotation of the knurled knob, a coil spring 610 located between the knob 602 and a collar 612, creates a drag which causes the clamp 604 to rotate in the same direction as the knob 602. Clamp rotation is achieved via an extended clamp shaft portion 614 of the shaft 608. Clamp rotation stops when a first end of the clamp 604 contacts a stop pin 616 shown in FIG. 6A. At this point, the threaded shaft 608 on the clamp is drawn down by the threads in the knob 602 and the tang is forced into the cavity and clamped in place.

When the knob 602 is rotated in a clockwise direction, the clamp 604 is raised by the threads of the shaft 608. When the clamp has raised sufficiently to release pressure on the tang 506, the drag of spring 610 causes the clamp 604 to rotate a predetermined amount (e.g., 90°) until an opposite end of the clamp 604 contacts the stop pin 616 as shown in FIG. 6C. As the operator continues to rotate the knob 602 clockwise, the clamp 604 is raised. When the clamp raises a predetermined distance, the collar 612 on the clamp shaft 614 contacts an ejection pin 618 (see FIG. 6D), and begins to raise the ejection pin. The ejection pin pushes the tang 506 up and out of the cavity. FIG. 6C shows the holder with the prosthetic blank or prosthetic model removed.

Figure 6E:
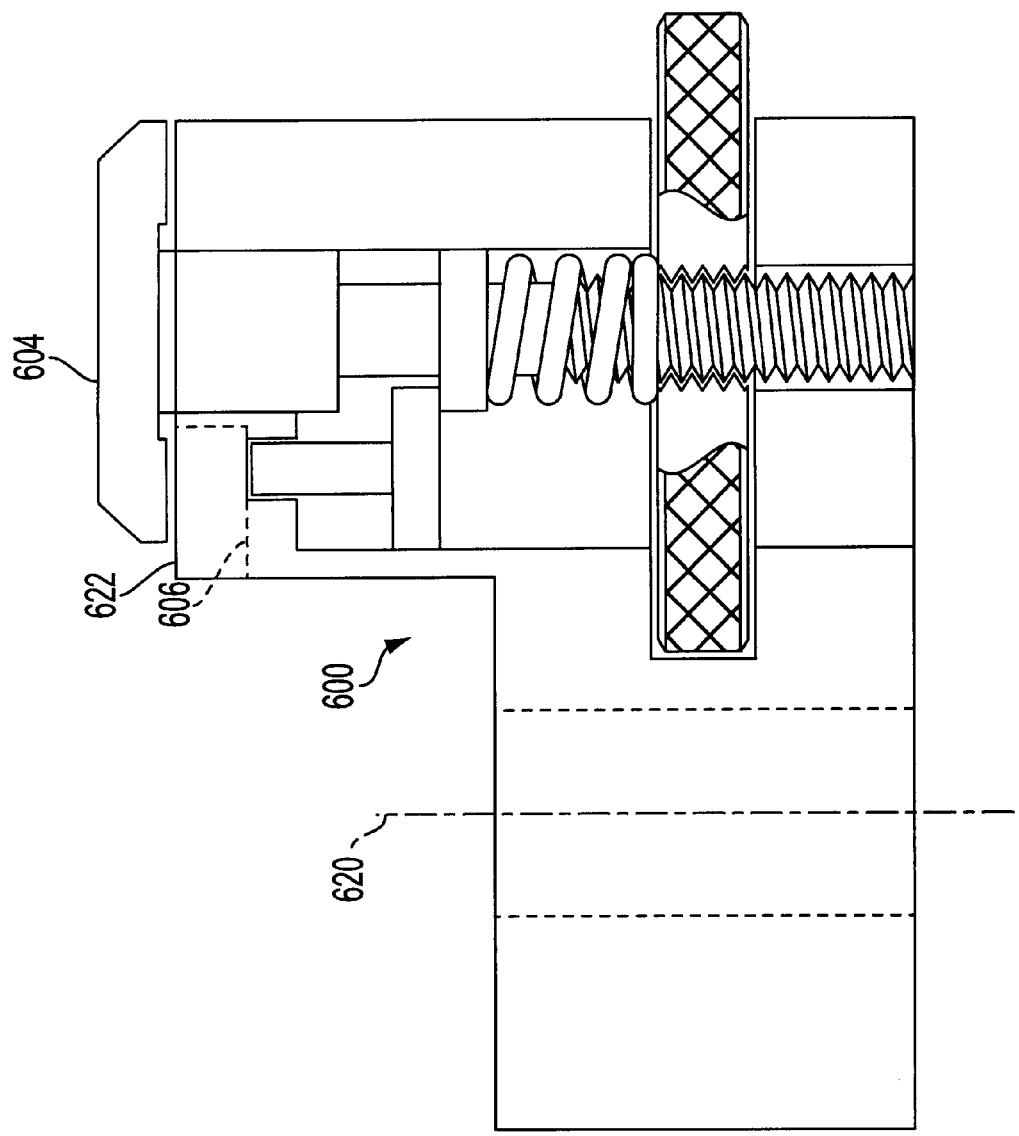

FIG. 6E shows that the holder 600 can be mounted to the copy milling apparatus of FIG. 3 about an axis 620 using any conventional mounting means (e.g., a screw and nut). In FIG. 6E, the tang of a dental prosthetic blank or model has been removed from recess 622.

Figure 7A:
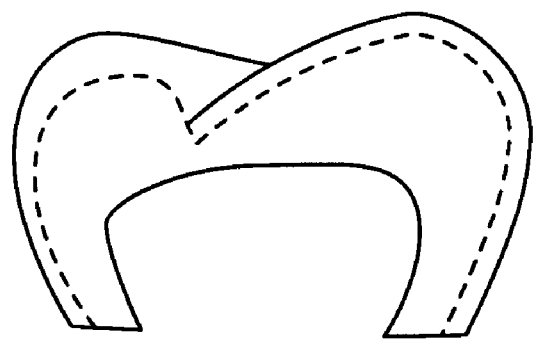
FIGS. 7A and 7B show an exemplary embodiment of a composite crown formed for use as a prosthetic dental blank and/or a dental prosthetic model.
Figure 7B:
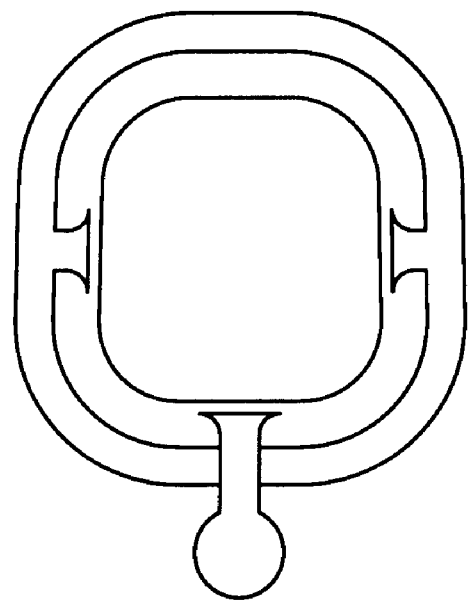

FIGS. 7A and 7B show a hybrid prosthetic blank configured as a crown in accordance with an exemplary embodiment of the present invention. Registration marks (e.g., T-shaped tang) are not shown in FIGS. 7A and 7B but can be used, as represented in FIGS. 5A–5C.

Generally speaking, an exemplary hybrid prosthetic blank can be configured with an outer material having a hardness comparable to or greater than that of human enamel, such as ceramic materials having a Knoop hardness in excess of 300 (although outer materials having Knoop hardnesses of less than 300 can be used). Exemplary materials suitable for the exterior ceramic of a hybrid prosthetic of the present invention are those available from Ivoclar Corporation of Switzerland, including, but not limited to those materials available under the name Targis™, and Empress™. Such materials, although providing high strength, are not as abrasive as materials such as porcelain, and are therefore preferred, although porcelain can be used.

Alternately, or in addition, the outer material can be selected as a function of its elastic modulus (i.e., stiffness). In accordance with exemplary embodiments, it is preferred for the outer material to have an increased stiffness with respect to the interior material. Again, in an exemplary embodiment, the stiffness of the outer material selected can be comparable to or greater than that of the human dentin (e.g., 16–18 gigapascals (GPa)), or lesser or greater. The materials already mentioned (i.e., Targis™, and Empress™) have stiffnesses of greater than 10 and 39, respectfully. Of course, materials with lesser stiffnesses can be used, although a stiffer support provides a stronger crown.

Alternately, the outer material can be selected on the basis of its strength, rated in megapascals (MPa). Again, the outer material can have a strength comparable to or greater than that of human dentin. The Targism™ material has a strength on the order of 157 MPa, and the Empress™ has a strength on the order of 130 MPa or better. Of course, materials having lesser strengths can be used, although stronger materials are preferred.

The inner material can be configured as a resin composite, or any other desired material which is acceptable for the milling to be performed. Those skilled in the art will appreciate that the ceramic and porcelain materials already mentioned are difficult to mill. This problem is avoided with the hybrid prosthetic blank having an interior material specifically selected for its ability to be easily shaped by a copy milling apparatus of the present invention.

In accordance with exemplary embodiments, the inner material, formed of a resin composite can have an elastic modulus, representing material stiffness, on the order of greater than 40 GPa, or lesser or greater. The resin composite can have a strength on the order of 100 MPa or lesser or greater.

Those skilled in the art will appreciate that the varying thicknesses of the outer and inner materials can be taken into account when selecting the properties of each respective material. For example, if a thicker, stronger resin is used as the inner material, then the outer material can be formed with reduced stiffness because of the added support the inner material will provide. The resin composite can be formed with any of a variety of particle fillers of the same or different materials. The composite structure can have a structure wherein stiffness is on the order of 15 to 100 GPa, or lesser or greater, and a composite strength on the order of 100–340 MPa, or lesser or greater.

The inner material can be bonded to the outer material using any known technique, including, but not limited to, the use of conventional bonding cements. The film thickness of the cement is a function of the inaccuracies produced in the crown, and can, for example, be on the order of 100 micrometers, or lesser or greater as desired.

Those skilled in the art will appreciate that a ceramic/porcelain material is a composite of glassy amorphous material with crystalline structure. As referenced herein, the term "ceramic" constitutes a material having approximately 30% crystalline structure or greater, with materials having less greater than 10% crystalline structure being referred to herein as "porcelain". In accordance with exemplary embodiments, the overall thickness of a dental prosthetic blank used, for example, in a typical prosthetic crown for a molar, can be approximately 4 millimeters (mm) in average thickness before milling, of which the outer material can be formed with an average thickness of 1.5 mm and the inner material which is to be milled can be formed with an average thickness of 2.5 mm. After milling, the outer material will, on average, constitute approximately 50% of the total thickness, and the inner material can be formed to constitute the remaining 50% of the overall thickness of the prosthetic. Those skilled in the art will appreciate that although the inner material is selected for its ability to be easily milled, if necessary, milling of the outer material to accommodate a particular fitting, can be performed.

An exemplary embodiment of a dental prosthetic blank as shown in FIGS. 7A and 7B can be formed to standardized dimensions, and milled in accordance with exemplary embodiments of the present invention. Referring to FIG. 7A, a cross sectional view of the crown is illustrated. FIG. 7B shows its hybrid structure, wherein an outer material 702 is formed of a hard ceramic or porcelain material, and the inner material is formed of a more easily millable, softer resin material.

Those skilled in the art will appreciate that although the exemplary dimension illustrated in FIG. 7B are selected for a molar prosthetic crown, these dimensions can be varied as desired to accommodate any prosthetic. For example, crowns used with respect to bicuspids, onlays or inlays, can be formed with outer/inner material thicknesses selected to accommodate the amount of milling, and the desired strength, hardness and stiffness of the prosthetic.

According to the present invention, once the dental prosthetic has been formed, and the tooth or teeth upon which the prosthetic is to be placed prepared, the prosthetic can be inserted into place. In accordance with exemplary embodiments, any technique used for cementing can be used. For example, a light cured cement can be used whereby the prosthetic is inserted into place and, after all adjustments have been made, is exposed to a relatively high intensity light to cure the cement. In addition, known techniques which improve seating of the prosthetic can be used, including techniques whereby small holes are inserted into the top of the prosthetic to allow cement to be released therefrom during placement of the prosthetic on the prepared tooth.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. An apparatus for producing a dental prosthetic comprising:

means for holding a dental prosthetic model and a dental prosthetic blank having exterior dimensions matched to those of said prosthetic model; and means for machining a three-dimensional surface of said dental prosthetic blank to match a three dimensional surface of said dental prosthetic model, said holding means being rotatable about at least a single axis, and said machining means having at least one arm mounted for linear, rotary motion on a linear axis, the at least one arm being slidable along and pivotable about the linear rotary axis.

2. An apparatus according to claim 1, wherein said machining means comprising:

an upper beam assembly which includes the at least one arm and a linear, rotary bearing, said upper beam assembly being slidable along and pivotable about said linear, rotary bearing.

3. An apparatus according to claim 2, wherein said upper bearing beam assembly includes:

the at least one arm slidable along and rotatable about said linear, rotary bearing;

a second arm rotatable about the at least one arm; and a bearing beam attached to said second arm to support a stylus for tracing said dental prosthetic model and a tool for cutting said dental prosthetic blank.

4. An apparatus according to claim 3, wherein said upper beam assembly includes:

means for adjusting a position of said at least one arm and said second arm to align said stylus and said tool with respect to said holding means.

5. An apparatus according to claim 1, comprising:

an adjustment means for adjustable alignment of the machining means and the holding means in at least one of a vertical plane and a horizontal plane.

6. An apparatus according to claim 1, in further combination with said dental prosthetic model, said dental prosthetic model comprising:

registration marks on external surfaces.

7. An apparatus according to claim 6, in further combination with said dental prosthetic blank, said dental prosthetic blank further including:

registration marks on external surfaces, the registration marks of said dental prosthetic blank being matched in location to the registration marks of said dental prosthetic model.

8. An apparatus according to claim 6, wherein said registration marks are formed as a "T" shaped tang which mates to a fixture used to register a position of said dental prosthetic model in said apparatus.

9. An apparatus according to claim 7, wherein said dental prosthetic blank and said dental prosthetic model include registration marks formed as "T" shaped tangs, said apparatus further including:

fixtures having surfaces which mate to said "T" shaped tangs of said dental prosthetic blank and said dental prosthetic model.

10. An apparatus according to claim 1, further comprising:

at least one counterforce for maintaining a set position of said machining means relative to said dental prosthetic model.

11. An apparatus according to claim 1, wherein a shape of the dental prosthetic model is matched to a shape of the dental prosthetic blank prior to machining the dental prosthetic blank.

12. A method for producing a dental prosthetic comprising the steps of:

providing a dental prosthetic model;

providing a dental prosthetic blank having exterior dimensions matched to those of said dental prosthetic model;

placing said dental prosthetic model and said dental prosthetic blank in holding fixtures for machining said dental prosthetic blank;

moving said holding fixture of said dental prosthetic blank in a single rotary axis; and moving a cutting tool supported on a linear rotary axis to mill said dental prosthetic blank.

* * * * *